(12) United States Patent
Li

(10) Patent No.: US 6,723,058 B2
(45) Date of Patent: *Apr. 20, 2004

(54) DEVICE AND METHOD FOR DETERMINING PARAMETERS OF BLIND VOIDS

(75) Inventor: Lehmann K. Li, Milford, CT (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/330,699

(22) Filed: Dec. 27, 2002

(65) Prior Publication Data

US 2003/0176814 A1 Sep. 18, 2003

Related U.S. Application Data

(63) Continuation of application No. 09/894,727, filed on Jun. 28, 2001, now Pat. No. 6,500,132.
(60) Provisional application No. 60/215,486, filed on Jun. 30, 2000.

(51) Int. Cl.$^7$ ................................................ A61B 5/107
(52) U.S. Cl. ........................ 600/594; 33/512; 128/898
(58) Field of Search ............................ 600/594, 587; 33/512, 511; 128/898

(56) References Cited

U.S. PATENT DOCUMENTS

| | | | |
|---|---|---|---|
| 3,918,164 A | 11/1975 | Krautmann | |
| 5,197,465 A | 3/1993 | Montgomery | |
| 5,471,756 A | 12/1995 | Bolanos et al. | |
| 5,823,974 A | 10/1998 | Grassi | |
| 6,224,599 B1 | 5/2001 | Baynham et al. | |
| 6,500,132 B1 * | 12/2002 | Li | 600/594 |

* cited by examiner

Primary Examiner—Kevin Lee
(74) Attorney, Agent, or Firm—Woodard, Emhardt, Moriarty, McNett & Henry LLP

(57) ABSTRACT

Device for determining the size of a blind void comprises an elongated rigid rod, an actuator slidably movable relative to the rod, the actuator having a distal end for insertion into the void, a distal flexible element fixed at one end thereof to the rod, a second flexible element fixed at one end thereof to the rod and proximally removed from the distal flexible element. Movement of the actuator is operative to cause equal movements of the distal end portions of the distal and proximal elements, to cause the distal element to bulge outwardly from the rod to engage interior walls of the void and to cause the proximal element to bulge outwardly in a configuration duplicative of the distal element bulge, the proximal element being outside of the void and subject to observation.

13 Claims, 4 Drawing Sheets

DEVICE AND METHOD FOR DETERMINING PARAMETERS OF BLIND VOIDS

REFERENCE TO PENDING PRIOR PATENT APPLICATION

This patent application is a continuation of pending U.S. patent application Ser. No. 09/894,727, filed Jun. 28, 2001, now U.S. Pat. No. 6,500,132 which claims the benefit of U.S. Provisional Patent Application Ser. No. 60/215,486, filed Jun. 30, 2000, the contents of each patent application hereby being incorporated herein by reference.

FIELD OF THE INVENTION

This invention relates to the field of surgical devices used primarily for the repair or replacement of human tissue, including, but not limited to, the nucleus pulposus of the spine. The invention further relates to the method of using such devices.

BACKGROUND OF THE INVENTION

The spinal column is a flexible chain of closely linked vertebral bodies. In a normal human spine there are seven cervical, twelve thoracic and five lumbar vertebral bodies. Below the lumbar vertebrae are the sacrum and coccyx. Each individual vertebra has an outer shell of hard, dense bone. Inside the vertebra is a honeycomb of cancellous bone containing red bone marrow. All of the red blood cells and many of the white blood cells are generated inside this cancellous bone, where the blood cells mature before being released into the blood circulation.

The spinal disc serves as a cushion between the vertebral bodies to permit controlled motion. A healthy disc consists of three components: a gelatinous inner core called the nucleus pulposus; a series of overlapping and laminated plies of tough fibrous rings called the annulus fibrosus; and two superior and inferior thin cartilage layers, connecting the disc to the thin cortical bone of the vertebral bodies, called the endplates.

The spinal disc may be displaced or damaged due to trauma or disease, such as a herniation or degenerative disc disease.

A herniated disc may bulge out and compress itself onto a nerve, resulting in lower leg pain, loss of muscle control, or paralysis. To treat a herniated disc, the offending nucleus portions are generally removed surgically.

Disc degeneration gradually reduces disc height, forcing the annulus to buckle, tear or separate radially or circumferentially, and causing persistent and disabling back pain. Degenerative disc disease is generally treated presently by surgically removing the nucleus and fusing the adjacent vertebral bodies to stabilize the joint.

In either case, whether removing a portion of the nucleus or all of the nucleus, these procedures ultimately place greater stress on adjacent discs to compensate for the lack of motion, which may cause premature degeneration of those adjacent discs.

Modern trends in surgery include the restoration of bodily function and form (i.e., repair) of anatomical structures through the use of minimally invasive surgical techniques. The ability to surgically repair damaged tissues or joints, creating as few and as small incisions as possible, produces less trauma, less pain and better clinical outcomes in general.

An emerging technique to treat degenerative disc disease is to replace the degenerated nucleus with a prosthetic nucleus in an attempt to restore function, versus fusion which severely limits the function of the spine. Since a degenerated nucleus can be removed using relatively small diameter instruments (e.g. 5 mm or less), this approach is more conducive to minimally invasive techniques.

A deficiency of current minimally invasive surgical techniques to replace the nucleus is the difficulty in determining whether enough space in the disc has been created to properly fit an implant. Creating the proper dimension cavity may be particularly important when implanting a device that expands, such as with a hydrogel implant. If the cavity created is larger than the implant, unintended implant movement or instability can occur. If the cavity created is smaller than the implant, an implant either may not fit, may not be positioned correctly or an expandable device may not achieve its proper functional shape.

SUMMARY OF THE INVENTION

It is, therefore, one object of the present invention to provide a device and method for determining how much space is created in human tissue, particularly when the space is in a visually impaired location.

A further object of the invention is to provide a device and method for determining how much space is created in the inner portion of the intervertebral disc space to facilitate the implantation of an artificial nucleus pulposus. The present invention is adapted to be placed through a small opening created in the annulus to minimize trauma to surrounding tissue.

With the above and other objects in view, a feature of the invention is the provision of a device for determining parameters of a blind void. The device comprises an elongated rigid rod, and an actuator extending lengthwise of the rod and slidably movable relative to the rod, the actuator having a distal end for insertion into the void. A first flexible element is fixed at one end thereof to the rod proximate the distal end of the rod. A second flexible element is fixed at one end thereof to the rod and proximally removed from the distal end of the rod and from the first element. Movement of the actuator is operative to cause equal movements of the distal end portions of the first and second elements, to cause the first element to bulge outwardly from the rod to engage interior walls of the void and to cause the second element to bulge outwardly in a configuration substantially duplicative of the first element bulge, the second element being outside of the void and subject to observation.

In accordance with a further feature of the invention, there is provided a method for determining parameters of a blind void, the method comprising the steps of providing a device comprising an elongated rigid rod, a first flexible element fixed at one end thereof to the rod proximate a distal end of the rod, a second flexible element fixed at one end thereof to the rod and proximally removed from the distal end of the rod and from the first element, and an actuator extending lengthwise of the rod and engageable with distal end portions of the first and second elements. The method further includes the steps of inserting the distal end of the actuator and the first element into the void, moving the actuator to cause movements of the distal end portions of the first and second elements, to cause the first element to bulge outwardly to engage interior walls of the void, and to cause the second element to bulge outwardly in a configuration duplicative of the first element bulge, the second element being outside of the void, and determining from the size of the second element the size of the first element and thereby the void.

The above and other features of the invention, including various novel details of construction and combinations of parts and method steps, will now be more particularly described with reference to the accompanying drawings and pointed out in the claims. It will be understood that the particular device and method embodying the invention are described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DETAILED DESCRIPTION OF THE PREFERRED EMBODIMENTS

Figure 1:
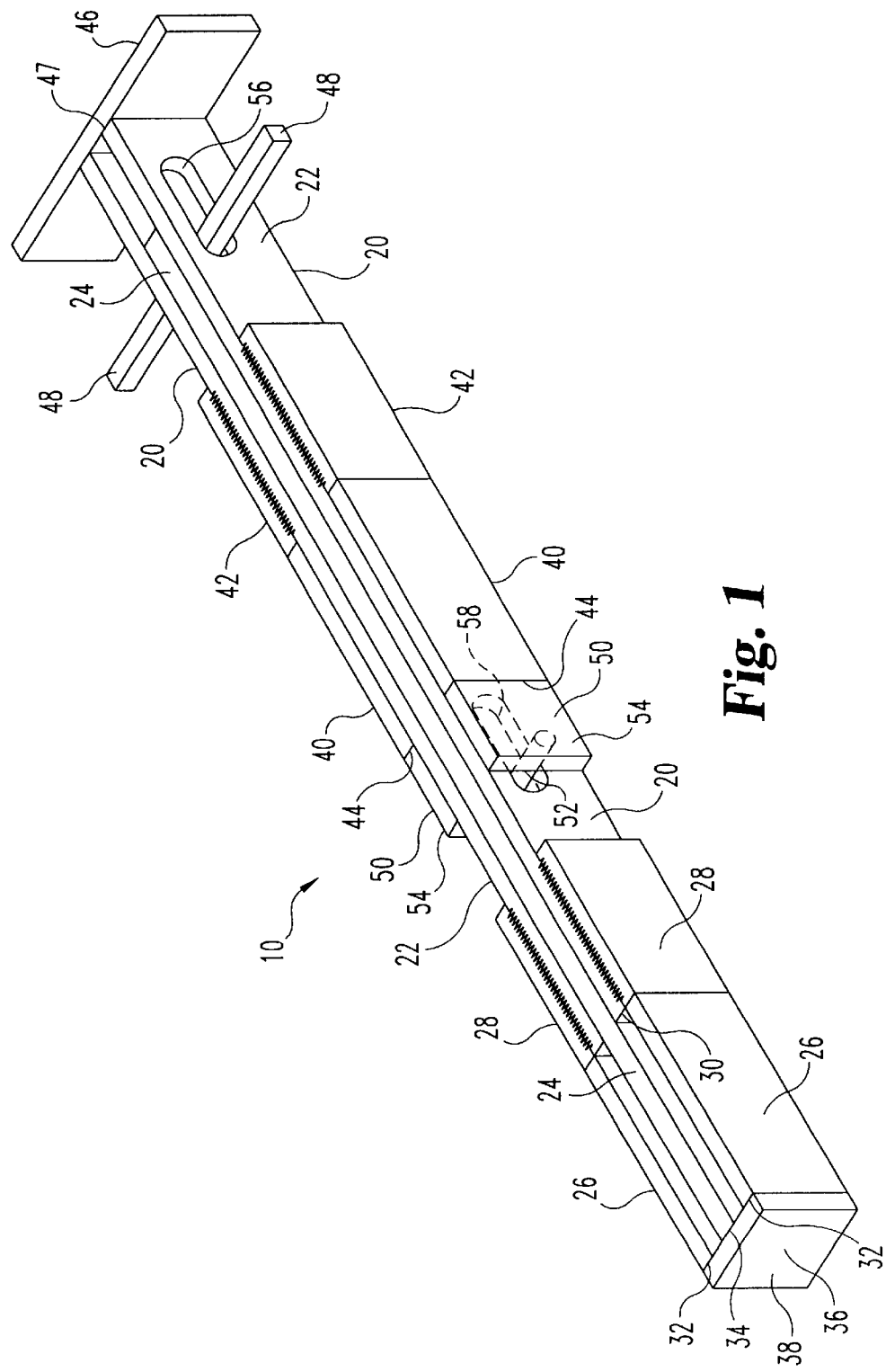
FIG. 1 is a perspective view of one form of device illustrative of an embodiment of the invention.

Referring to FIG. 1, it will be seen that an illustrative inventive device 10 includes an elongated rigid rod 20, in the form of at least one, and preferably two, plates 22. When the device includes two plates, the plates extend parallel to each other.

An actuator 24 extends lengthwise of the rod 20 and is slidably movable relative to the rod 20. When the rod 20 includes two plates 22, the actuator 24 is slidably disposed between the two plates.

A first flexible element, such as a strip 26, is fixed at a proximal end portion 28 thereof to the rod 20 proximate the distal end 30 of the rod. The element 26 may be a bendable strip of metal having a distal free end 32. A first flexible element 26 is fixed to each of the plates 22.

Mounted on a distal end 34 of the actuator 24 is a first engagement member 36 which is engageable with the distal end 32 of each of the first elements 26. The first engagement member 36 may be an end-piece 38 fixed to the distal end 34 of the actuator 24.

A second flexible element, such as a strip 40, is fixed to each of the plates 22 at a proximal end portion 42 of the element. The element 40 is of the same configuration, size and material as the element 26 and is provided with a distal free end 44. A flexible second element 40 is fixed to each of the plates 22 proximally of the distal end 30 of the rod 20 and proximally of the first flexible element 26.

Mounted on each of the plates 22 on a side opposite from the actuator 24 is a second engagement member 50 connected to the actuator 24 by a connecting pin 52. The second engagement member 50 may be a block 54.

The rod 20 is provided with a grip portion 46 at the proximal end 47 of the rod by which the rod may be gripped by an operator (not shown). The actuator 24 is provided with a manipulable portion, such as a cross-bar 48, such that an operator may hold the device 10 in one hand by gripping the rod grip portion 46 and the actuator cross-bar 48, and by squeezing the cross-bar toward the grip portion, cause the actuator to move proximally relative to the plates 22. The plates are each provided with a slot 56 through which extends a cross-bar portion, such that the cross-bar 48 may readily move relative to plates 22. Similarly, the plates 22 are each provided with a slot 58 through which extends the connecting pin 52, permitting movement of the engagement block 54 relative to the plates 22.

Figure 2:
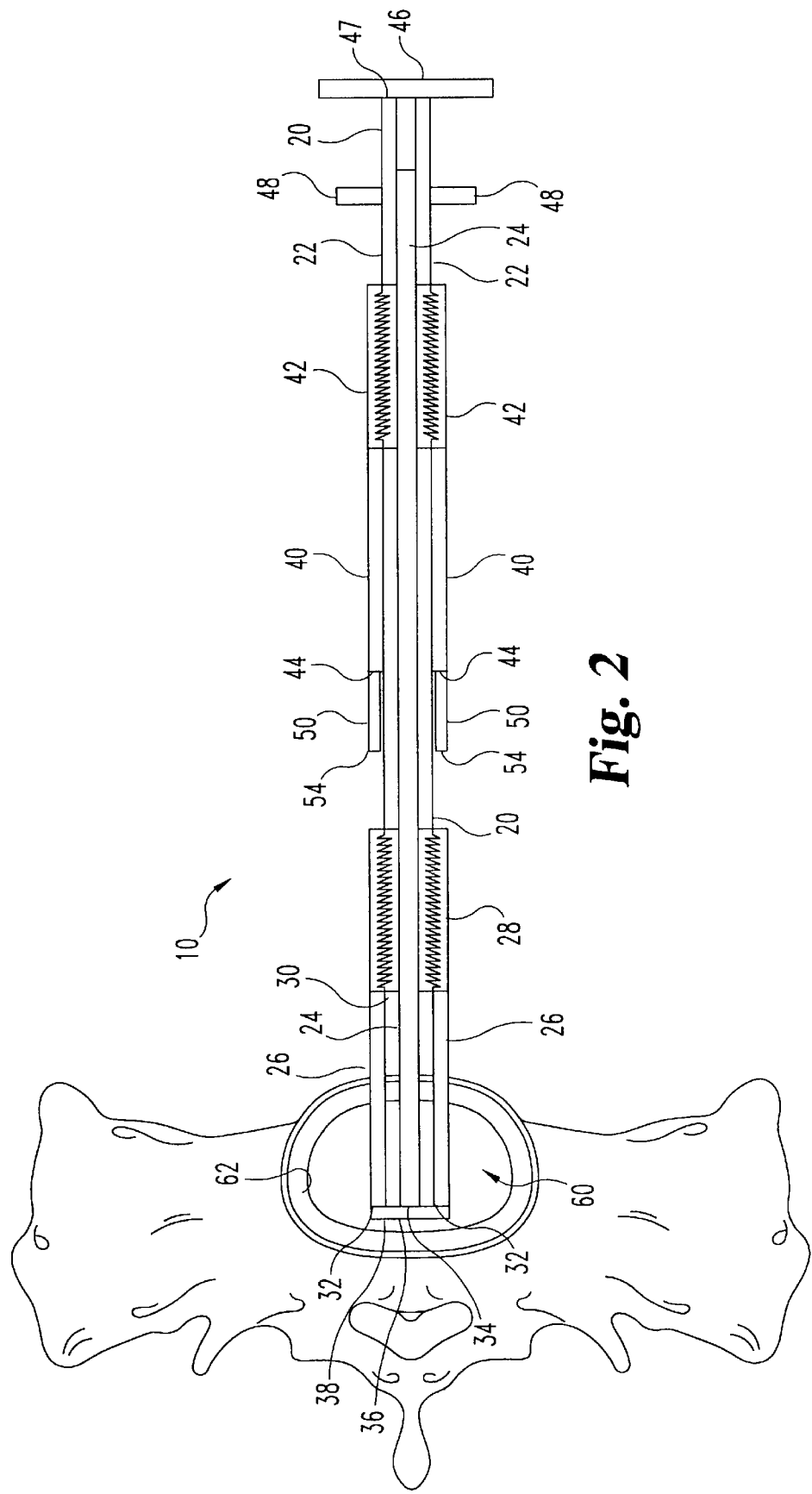
FIG. 2 is a diagrammatic top view of the device of FIG. 1 deployed in a spinal disc.
Figure 3:
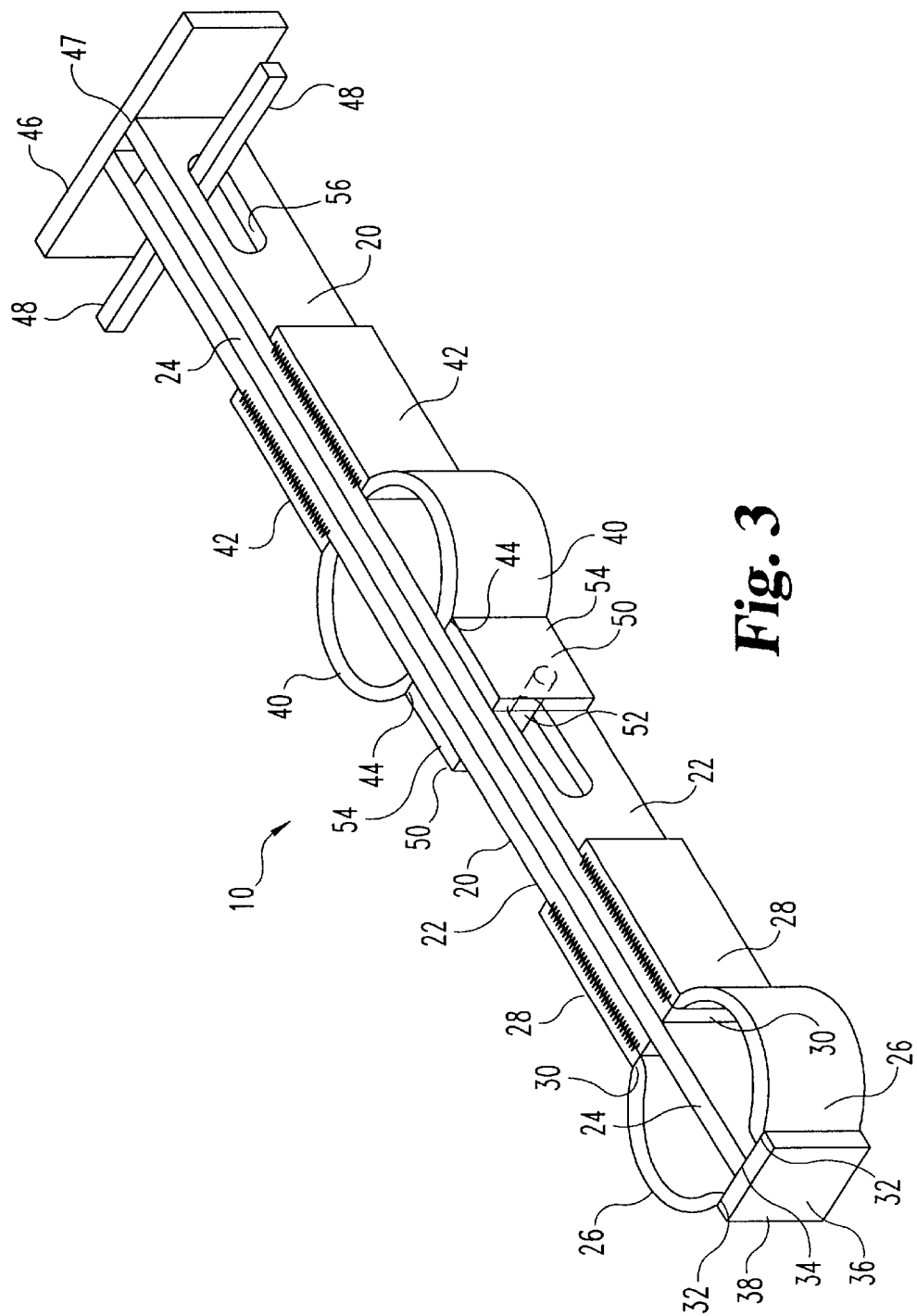
FIG. 3 is similar to FIG. 1, but shows the device in another operative configuration.
Figure 4:
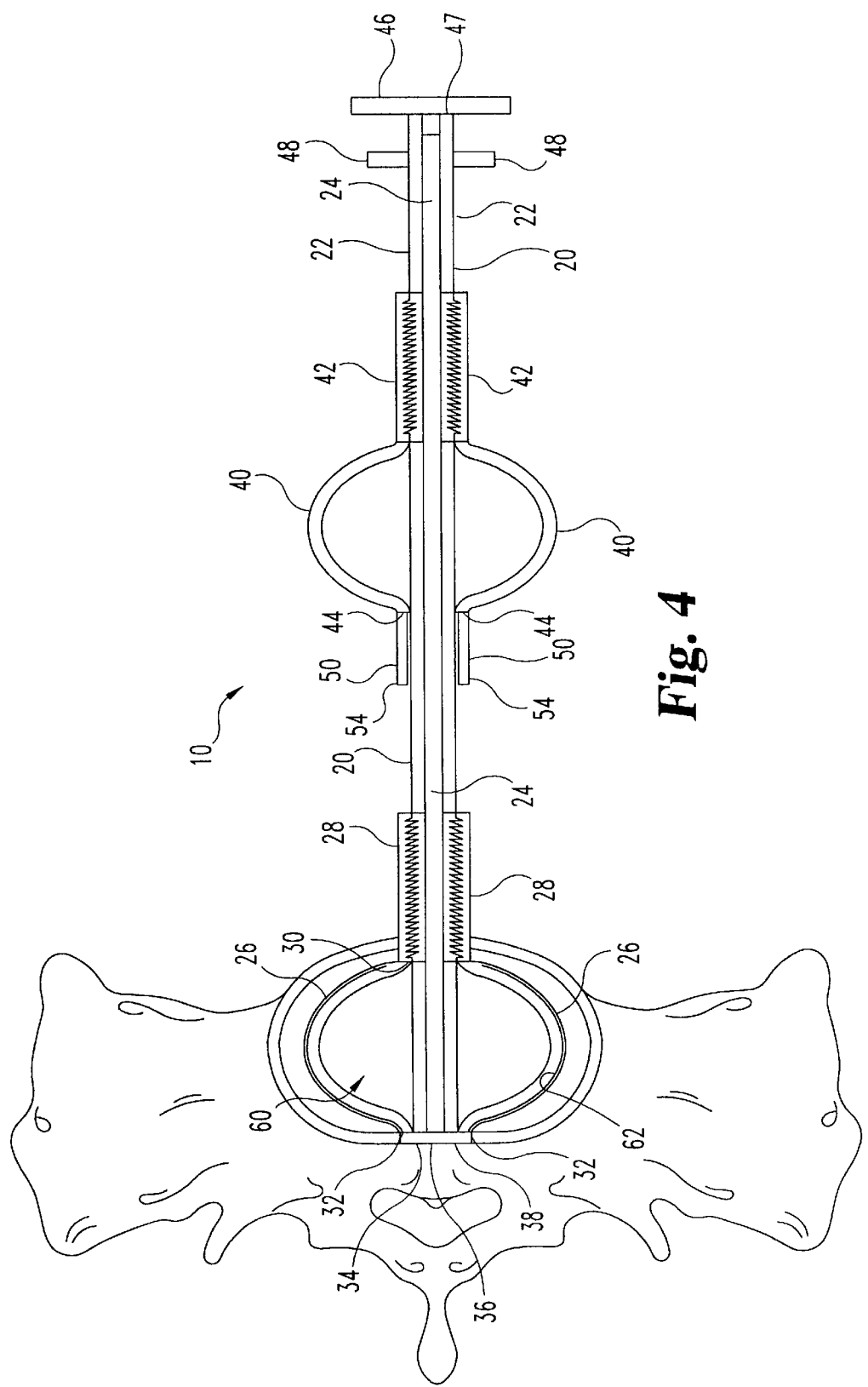
FIG. 4 is similar to FIG. 2, but shows the device in a parameter determining configuration.

In operation, the device 10, as shown in FIG. 1, is inserted into a void, such as a spinal disc cavity 60 from which the nucleus pulposus has been removed (FIG. 2). By manipulation of the rod grip portion 46 and actuator cross-bar 48, the actuator 24 is made to move proximally relative to the rod 20. Proximal movement of the actuator 24 carries with it proximal movement of the end piece 38 and engagement block 54 which, contacting the element free distal ends 32, 44, respectively, cause proximal movement of the flexible element free ends 32, 44, while the flexible element proximal ends 28, 42 remain fast to their respective plates 22. The elements are thus caused to bulge outwardly (FIGS. 3 and 4) until the first element 26 engages interior walls 62 of the cavity 60, stopping movement of the actuator 24.

At this point, the first element 26 is hidden from view and the extent of the bulge is not ordinarily observable. However, because the second flexible element 40 is of the same configuration, size and material as the first element and expands in a manner duplicating the expansion of the first element, and is in an observable disposition, the size of the spinal disc cavity may be determined by observation of the second element. While it is intended that "observation" includes visual observation and mechanical measurement, it is apparent that "observation" can be undertaken by optical or automatic data gathering instruments in combination with computers and/or read-out devices.

It should also be appreciated that device 10 may be used to determine cavity sizes in a variety of different directions. Thus, for example, in FIGS. 2–4, device 10 is shown oriented so as to measure cavity size in a substantially horizontal direction. However, it should also be appreciated that device 10 may be oriented, or modified, so as to measure cavity size in a substantially vertical direction, or in some other direction.

There is thus provided a device and method for determining the space available in a blind void, and particularly in a spinal disc cavity vacated by extraction of the nucleus pulposus therefrom.

It is to be understood that the present invention is by no means limited to the particular construction herein disclosed and/or shown in the drawings, but also comprises any modification or equivalent within the scope of the claims.

What is claimed is:

1. A device for determining a parameter of a blind void, comprising:

an elongate member extending along an axis and including a first flexible element and a second flexible element axially offset from said first flexible element, said first flexible element having an initial configuration suitable for insertion into the blind void; and an actuator member coupled to said first and second flexible elements and adapted to transition said first flexible element from said initial configuration to a deformed configuration corresponding to a parameter of the blind void and to transition said second flexible element to a deformed configuration corresponding to said deformed configuration of said first flexible element.

2. The device of claim 1, wherein relative displacement between said actuator member and said elongate member transitions said first and second flexible elements toward said deformed configurations.

3. The device of claim 2, wherein said relative displacement comprises relative linear displacement generally along said axis.

4. The device of claim 1, wherein said deformed configurations of said first and second flexible elements comprise outwardly buckled portions.

5. The device of claim 1, wherein said deformed configuration of said first flexible element corresponds to a size and shape of the blind void.

6. The device of claim 5, wherein said deformed configuration of said first flexible element engages interior peripheral walls surrounding the blind void.

7. The device of claim 1, wherein said second flexible element has an initial configuration substantially similar to said initial configuration of said first flexible element.

8. A method for determining a parameter of a blind void, comprising:

providing an elongate member extending along an axis and including a first flexible element and a second flexible element axially offset from the first flexible element;

inserting the first flexible element into the blind void while in an initial configuration;

transitioning the first flexible element to a deformed configuration corresponding to a parameter of the blind void; and transitioning the second flexible element to a deformed configuration corresponding to the deformed configuration of the first flexible element.

9. The method of claim 8, further comprising:

providing an actuator member adapted to transition the first and second elements to the deformed configurations; and displacing the actuator member relative to the first and second flexible elements to facilitate the transitioning.

10. The method of claim 8, further comprising determining the approximate size and shape of the blind void by observing the size and shape of the deformed configuration of the second flexible element.

11. The method of claim 8, wherein the transitioning comprises outward buckling.

12. The method of claim 8, further comprising:

reforming the first flexible element back toward the initial configuration; and removing the first flexible element from the blind void.

13. A device for determining the size of a blind void created by removal of at least a portion of the nucleus pulposus of a spinal disc, comprising:

means for measuring a parameter of the blind void; and means for indicating the measured parameter at a location remote from the blind void.

* * * * *